United States Patent
Afifi (10) Patent No.: US 10,853,939 B2
(45) Date of Patent: Dec. 1, 2020

(54) SYSTEM AND METHOD FOR DIAGNOSIS AND ASSESSMENT OF DISC DERANGEMENT DISORDERS

(71) Applicant: Maryam Afifi, Rancho Cucamonga, CA (US)

(72) Inventor: Maryam Afifi, Rancho Cucamonga, CA (US)

(*) Notice: Subject to any disclaimer, the term of this patent is extended or adjusted under 35 U.S.C. 154(b) by 1248 days.

(21) Appl. No.: 15/055,285

(22) Filed: Feb. 26, 2016

(65) Prior Publication Data

US 2016/0249850 A1 Sep. 1, 2016

Related U.S. Application Data (60) Provisional application No. 62/121,107, filed on Feb. 26, 2015.

(51) Int. Cl.
   G06T 7/00 (2017.01)
   A61B 6/00 (2006.01)
   (Continued)

(52) U.S. Cl.
   CPC ............ *G06T 7/0012* (2013.01); *A61B 5/004* (2013.01); *A61B 5/1121* (2013.01);
   (Continued)

(58) Field of Classification Search
   CPC ......... G06T 7/0012; G06T 7/174; G06T 7/50; G06T 7/77; G06T 7/246; G06T 7/143;
   (Continued)

(56) References Cited

U.S. PATENT DOCUMENTS

| | | | | |
|---|---|---|---|---|
| 5,267,293 A | * | 11/1993 | Virta | ............... A61B 6/14 378/38 |
| 2002/0048741 A1 | * | 4/2002 | Jordan | ............... A61C 13/0003 433/73 |

(Continued)

OTHER PUBLICATIONS

Al-koshab et al. "Assessment of Condyle and Glenoid Fossa Morphology Using CBCT in Southeast Asians." PLoS ONE 10(3). Mar. 24, 2015. (Year: 2015).*

(Continued)

*Primary Examiner* — Amanda Lauritzen Moher
(74) *Attorney, Agent, or Firm* — Cohen IP Law Group, P.C.; Michael N. Cohen (57) ABSTRACT

A method and system for assessing disc derangement disorders (DDD) in patients comprises an image scanning module, a DDD screening system and a diagnosis and assessment module. The DDD screening system is in communication with the image scanning module via a network. The DDD screening system includes an application server residing on a computer having a processor installed with a disc derangement disorders (DDD) screening application and coupled with a memory unit integrated with a central database. The DDD screening application provides a set of statistical probability data of the at least one image utilizing a normalized measurement of at least one image to a diagnosis and assessment module. The diagnosis and assessment module generates a report that allows the DDD system to evaluate the presence or absence of DDD based on the statistical probabilities.

10 Claims, 10 Drawing Sheets

(51) Int. Cl.

| | | |
|---|---|---|
| *A61B 5/00* | (2006.01) | |
| *A61B 6/03* | (2006.01) | |
| *A61B 6/14* | (2006.01) | |
| *G06K 9/48* | (2006.01) | |
| *G06K 9/00* | (2006.01) | |
| *G06T 9/00* | (2006.01) | |
| *G06T 7/10* | (2017.01) | |
| *G06T 7/13* | (2017.01) | |
| *G06T 7/143* | (2017.01) | |
| *G06T 7/246* | (2017.01) | |
| *G06T 7/174* | (2017.01) | |
| *G06T 7/50* | (2017.01) | |
| *G06T 7/77* | (2017.01) | |
| *A61B 5/11* | (2006.01) | |
| *G16H 30/20* | (2018.01) | |
| *G06T 7/62* | (2017.01) | |
| *G16H 30/40* | (2018.01) | |
| *A61C 9/00* | (2006.01) | |
| *A61C 11/00* | (2006.01) | |
| *G16H 50/20* | (2018.01) | |
| *G06T 9/20* | (2006.01) | |
| *G01B 11/25* | (2006.01) | |
| *G06T 7/55* | (2017.01) | |
| *G01B 11/00* | (2006.01) | |
| *G06T 7/60* | (2017.01) | |
| *G06T 7/12* | (2017.01) | |

(52) U.S. Cl.
CPC .......... *A61B 5/1128* (2013.01); *A61B 5/4514* (2013.01); *A61B 5/4542* (2013.01); *A61B 6/032* (2013.01); *A61B 6/14* (2013.01); *A61B 6/4085* (2013.01); *A61C 9/004* (2013.01); *A61C 11/00* (2013.01); *G06K 9/00* (2013.01); *G06K 9/48* (2013.01); *G06T 7/0002* (2013.01); *G06T 7/10* (2017.01); *G06T 7/13* (2017.01); *G06T 7/143* (2017.01); *G06T 7/174* (2017.01); *G06T 7/246* (2017.01); *G06T 7/50* (2017.01); *G06T 7/62* (2017.01); *G06T 7/77* (2017.01); *G06T 9/00* (2013.01); *G16H 30/20* (2018.01); *G16H 30/40* (2018.01); *G16H 50/20* (2018.01); *A61B 5/4533* (2013.01); *G01B 11/00* (2013.01); *G01B 11/25* (2013.01); *G06K 9/481* (2013.01); *G06T 7/0014* (2013.01); *G06T 7/12* (2017.01); *G06T 7/55* (2017.01); *G06T 7/60* (2013.01); *G06T 9/20* (2013.01); *G06T 2207/10072* (2013.01); *G06T 2207/30036* (2013.01)

(58) Field of Classification Search
CPC .......... G06T 7/13; G06T 7/0002; G06T 7/10; G06T 9/00; G06T 7/0014; G06T 7/12; G06T 7/60; G06T 7/55; G06T 9/20; G06T 2207/10072; G06T 2207/30036; G16H 30/20; G16H 50/20; G16H 30/40; A61C 11/00; A61C 9/004; G06K 9/481; G06K 9/48; G06K 9/00; G01B 11/25; G01B 11/00; A61B 5/4533; A61B 5/004; A61B 5/1121; A61B 5/1128; A61B 5/4542; A61B 6/4085; A61B 5/4514; A61B 6/032; A61B 6/14
See application file for complete search history.

(56) References Cited

U.S. PATENT DOCUMENTS

| | | | |
|---|---|---|---|
| 2004/0170308 A1* | 9/2004 | Belykh | G06T 5/007 382/128 |
| 2005/0116946 A1* | 6/2005 | Chung | G06T 1/20 345/418 |
| 2012/0107763 A1* | 5/2012 | Adams | A61B 1/24 433/29 |
| 2013/0004042 A1* | 1/2013 | Yang | G06T 11/005 382/131 |

OTHER PUBLICATIONS

Hodges et al. "Impact of cone-beam computed tomography on orthodontic diagnosis and treatment planning." American Journal of Orthodontics and Dentofacial Orthopedics 143(5). May 2013. (Year: 2013).*
Bag et al. "Imaging of the temporomandibular joint: An update." World Journal of Radiology 6(8). Aug. 28, 2014. (Year: 2014).*
Honey et al. "Accuracy of cone-beam computed tomography imaging of the temporomandibular joint: Comparisons with panoramic and linear tomography." American Journal of Orthodontics and Dentofacial Orthopedics. Oct. 2007. (Year: 2007).*
Chinea S. "The effect of cone beam computed tomography (CBCT) imaging on orthodontic diagnosis and treatment planning." M.Sc. Thesis, University of Southern California. 2011. (Year: 2011).*
Khojastepour et al. "Comparison between Glenoid Fossa Roof Thickness in TMD and non-TMD Patients, a CBCT Study." J Dent Shiraz Univ Med Sci Sep. 2019 20(3): 165-170.*

* cited by examiner

| Normalized Measurements | TMJ Morphology Classifications |
|---|---|
| Angle Θ | Posterior slope of articular eminence |
| Line 6 / Line 2$_{modified}$ | Anterior aspect of glenoid fossa height/width ratio |
| Line 4 / Line 3 | Posterior aspect of articular eminence width/height ratio |
| Line 9 / Line 8$_{modified}$ | Mandibular condyle height/width ratio |
| Line ML / Line AP | Condylar head mediolateral dimension/ Anterioposterior dimension ratio |
| Angle β / Angle α | Mandibular condyle posterior angle/anterior angle ratio |

FIG. 8

| Disc Derangement Disorders | | | | |
|---|---|---|---|---|
| Product Capabilities | Clinical Exam | Jaw Tracker | MRI | CBCT → Software |
| 1. Definitive Diagnosis (POSITIVE RESULT) | Yes | Yes | Yes | Yes |
| a. Measures Severity Level | No | No | No | Yes |
| 2. Confirms Absence of DDD (NEGATIVE RESULT) | No | No | Yes | Yes |
| a. Measures Potential Risk Level (PREVENTATIVE) | No | No | No | Yes |
| 3. Time Frame | 10-15 min | 5-10 min | 30-45 min | 5-7 min |
| 4. Availability in Dental Office | Yes | Selected Offices | No | Yes |
| 5. Applicable for Patients with Pacemaker Devices | Yes | Yes | No | Yes |
| 6. Cost Range | $50-100 | $200-300 | $300-450 | $50-150 |

FIG. 9

SYSTEM AND METHOD FOR DIAGNOSIS AND ASSESSMENT OF DISC DERANGEMENT DISORDERS

CROSS-REFERENCE TO RELATED APPLICATIONS

This application claims the benefit of the U.S. Provisional Application 62/121,107 filed on Feb. 26, 2015.

STATEMENT REGARDING FEDERALLY SPONSORED RESEARCH AND DEVELOPMENT

Not Applicable.

FIELD OF THE DISCLOSURE

The present embodiment relates to the field of dentistry, and more particularly to a system for assessing disc derangement disorders (DDD) in patients with temporomandibular joint disorders (TMD) or TMD-like symptoms, with the additional capability of predicting the likelihood of DDD and detecting early signs of DDD in dental patients.

DISCUSSION OF RELATED ART

The temporomandibular joint (TMJ) differs from other joints of the body primarily by its sliding function and having joint surfaces along with a disc of fibrocartilage. The TMJ acts like a sliding hinge, connecting the jawbone to the skull. TMJ disorders (TMDs) cause pain in the jaw joint and in the muscles that control jaw movement. TMDs include muscle disorders and/or joint abnormalities such as disc displacement. Joint sounds, joint pain, and/or restricted mandibular motion may accompany alterations in the position of the TMJ disc. The anterior displacement of the disc is the most common TMD.

A conventional method for detecting and analyzing joint disorders utilizes an acoustic signal processing technique. However, such a method is not well-suited for the evaluation of unilateral/bilateral anterior disc displacement that pertains to the morphology of an articular eminence, a glenoid fossa, or a mandibular condyle. Moreover, such a method does not allow the proper determination of the impact of dental modifications on the TMJ.

Attempts have been made to compensate for these drawbacks by utilizing computer technology. The methods for determining the impact of a proposed dental modification on the TMDs utilizes computer technology for image-assisted risk assessment/evaluation of proposed dental treatments to obtain information relating to that impact. However, static imaging does not permit an accurate assessment of actual joint function, and the method lacks a system that includes a measurable index to analyze the functioning of the TMJ in patients.

Conventional TMDs diagnostic methods utilize one or more features to manage or reduce pain, discomfort, and other symptoms associated with TMDs. These symptoms range from mild to severe, and include headaches, facial pain, as well as pain and cracking in the jaw. For a given case, any one of these symptoms may be experienced either alone or as a combination of symptoms. Moreover, these symptoms may be indicative of conditions other than TMD. Consequently, proper diagnosis of TMDs is difficult. TMD diagnosis is further complicated by the fact that there is a lack of scientific inquiry into the etiologic or underlying cause of TMDs. As such, there remains a need for more effective ways to manage TMDs.

Therefore, there is a need for an improved system for DDD detection and assessment in patients with TMD or TMD-like symptoms. Such a needed system would evaluate the input image to analyze DDD in dental patients. Furthermore, such a needed system would provide a measurable statistical probability data that utilizes a normalized, mathematical-based strategy to assess unilateral/bilateral anterior disc displacement that pertains to the morphology of an articular eminence, a glenoid fossa, and a mandibular condyle. This system would provide a method to evaluate a severity level assessment, a potential risk level and to confirm normality according to statistical indicators. This system would be capable of providing evidence-based research to generate statistical probabilities to evaluate future cases. Finally, this system would have the capability to evaluate the contour of a condylar neck, a plurality of dimensions of a condylar head and a glenoid fossa, and the posterior slope of an articular eminence based on morphological differences of the TMJ in males and females with DDD. The present embodiment overcomes these shortcomings and accomplishes critical objectives.

SUMMARY OF THE DISCLOSURE

The present embodiment is a system for assessing disc derangement disorders (DDD) in patients with temporomandibular joint disorders (TMD) or TMD-like symptoms in addition to predicting the likelihood of DDD and/or detecting early signs of DDD in dental patients. The system comprises an image scanning module, an disc derangement disorders (DDD) screening system and a diagnosis and assessment module. The DDD screening system is in communication with the image scanning module via a network. The DDD screening system including an application server resides on a computer having a processor installed with a disc derangement disorders (DDD) screening application and coupled with a memory unit integrated to at least one central database. The DDD screening system is configured to load at least one image of a temporomandibular joint (TMJ) of the patient received from an image scanning module into the DDD screening application. The DDD screening system evaluates the at least one image to analyze a unilateral/bilateral anterior disc displacement with/without reduction that pertaining to the morphology of an articular eminence, a glenoid fossa, and a mandibular condyle. The system generates a diagnosis and assessment report at diagnosis and assessment module utilizing a normalized mathematical-based strategy of the DDD screening system to assess unilateral/bilateral anterior disc displacement with/without reduction as it pertains to the morphology of an articular eminence, a glenoid fossa, and a mandibular condyle. Moreover, an index probability module allows the DDD screening system to evaluate a contour of a condylar neck, a plurality of dimensions of a condylar head and a glenoid fossa, and a posterior slope of an articular eminence based on morphological differences of the TMJ in males and females with anterior disc displacement.

The image scanning module configured to provide the at least one image of the TMJ of the patient into the DDD screening system via the disc derangement disorders (DDD) screening application. The DDD screening application further comprises a calibrate measurement scale module, an adjust pixelation gradient module, an identification module, an angle-line measuring module, a calculation module, a normalization module, a first archive data module, an index probability module, a second archive data module and a diagnosis and assessment module. The calibrate measurement scale module and adjust pixelation gradient module enables a measurement scale to calibrate a maximum pixelation level of the at least one image to provide an accurate measurement. The identification module, the angle-line measuring module and the calculation module determines a measurable critical points and ratios of the at least one image. The normalization module generates a normalized measurement of the at least one image and stores in the first archive data module for future research purposes. The normalization process involves geometrical standardization of a measurement protocol, which is factored into an index design, and conversion of critical measureable components into proportions. The presence and absence of the DDD in the dental patients are evaluated by the index probability module which provides a set of statistical probability data of the at least one image and stores in the second archive data module for generating a diagnosis and assessment report at the diagnosis and assessment module.

The present invention discusses a morphological pattern of the TMJ according to gender differences. The gender differences play a significant role in the S*R interaction for anterior disc displacement. In other words, the levels of reduction (with or without) and symmetry (unilateral or bilateral paired with like verses bilateral paired with non-like) interact with each other to influence the dependent variables in specific ways. The dependent variables include the posterior slope of the articular eminence, the anterior aspect of the glenoid fossa height/width ratio, the posterior aspect of the articular eminence width/height ratio, the mandibular condyle height/width ratio, the condylar head mediolateral (ML) dimension/anterioposterior (AP) dimension ratio, and the mandibular condyle posterior angle/anterior angle ratio. The significance of the S*R interaction is recognized when gender was factored into the study design as the third factor with two levels: males and females. The differences between males and females are evaluated in two-way interaction between the two factors: symmetry and reduction. The morphological differences of the TMJ in males and females who have anterior disc displacement are evaluated. The morphological features of the TMJ to consider in DDD are the posterior slope of the articular eminence, the dimensions of the condylar head, namely its height/width as well as ML/AP dimensions, and the contour of the condylar neck, defined as the posterior angle/anterior angle of the mandibular condyle.

Other features and advantages of the present invention will become apparent from the following more detailed description, taken in conjunction with the accompanying drawings, which illustrate, by way of example, the principles of the invention.

DETAILED DESCRIPTION OF THE PREFERRED EMBODIMENT

The following describes example embodiments in which the present invention may be practiced. This invention, however, may be embodied in many different ways, and the description provided herein should not be construed as limiting in any way. Among other things, the following invention may be embodied as methods or devices. As such, the present invention may take the form of an entirely hardware embodiment, an entirely software embodiment, or an embodiment combining software and hardware aspects. The following detailed descriptions should not be taken in a limiting sense.

In this document, the terms "a" or "an" are used, as is common in patent documents, to include one or more than one. In this document, the term "or" is used to refer to a nonexclusive "or," such that "A or B" includes "A but not B," "B but not A," and "A and B," unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

Figure 1:
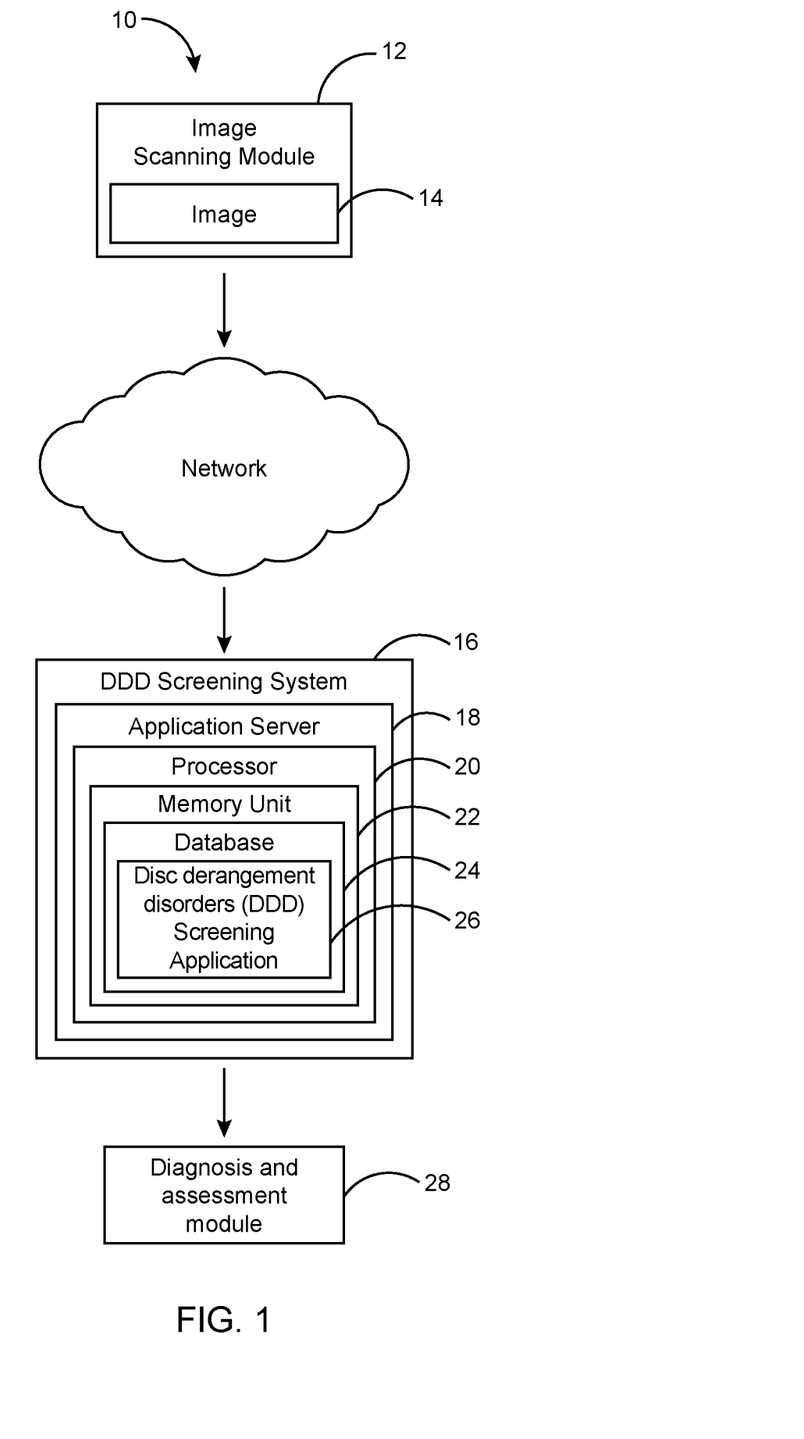
FIG. 1 illustrates a block diagram of a system in accordance with a preferred embodiment of the present invention.

Referring to FIG. 1, a block diagram of a system 10 in accordance with a preferred embodiment of the present invention is illustrated. The system 10 for disc derangement disorders (DDD) in patients. The system 10 comprises an image scanning module 12, a disc derangement disorders (DDD) screening system 16 and a diagnosis and assessment module 28. The DDD screening system 16 is in communication with the image scanning module 12 via a network, the DDD screening system 16 includes an application server that resides on a computer having a processor 20 installed with a disc derangement disorders (DDD) screening application 26 and coupled with a memory unit 22 integrated to at least one central database 24, the DDD screening system 16 is configured to load at least one image 14 of a temporomandibular joint (TMJ) of the patient received from an image scanning module 12 into the DDD screening application 26. The image scanning module 12 is selected from a group consisting of cone beam computed tomography (CBCT) and Magnetic Resonance Imaging (MRI) images, one in sagittal view and the other in the coronal view of the TMJ.

The DDD screening system 16 evaluates the at least one image 14 to analyze a unilateral/bilateral anterior disc displacement with/without reduction that pertaining to the morphology of an articular eminence, a glenoid fossa, and a mandibular condyle. The system 10 generates a diagnosis and assessment report at diagnosis and an assessment module 50 utilizing a normalized mathematical-based strategy of the DDD screening system 16 to assess unilateral/bilateral anterior disc displacement. Moreover, an index probability module 24 in the DDD screening system 16 allows to evaluate a contour of a condylar neck, a plurality of dimensions of a condylar head and a glenoid fossa, and a posterior slope of an articular eminence based on morphological differences of the TMJ in males and females with anterior disc displacement.

Figure 2:
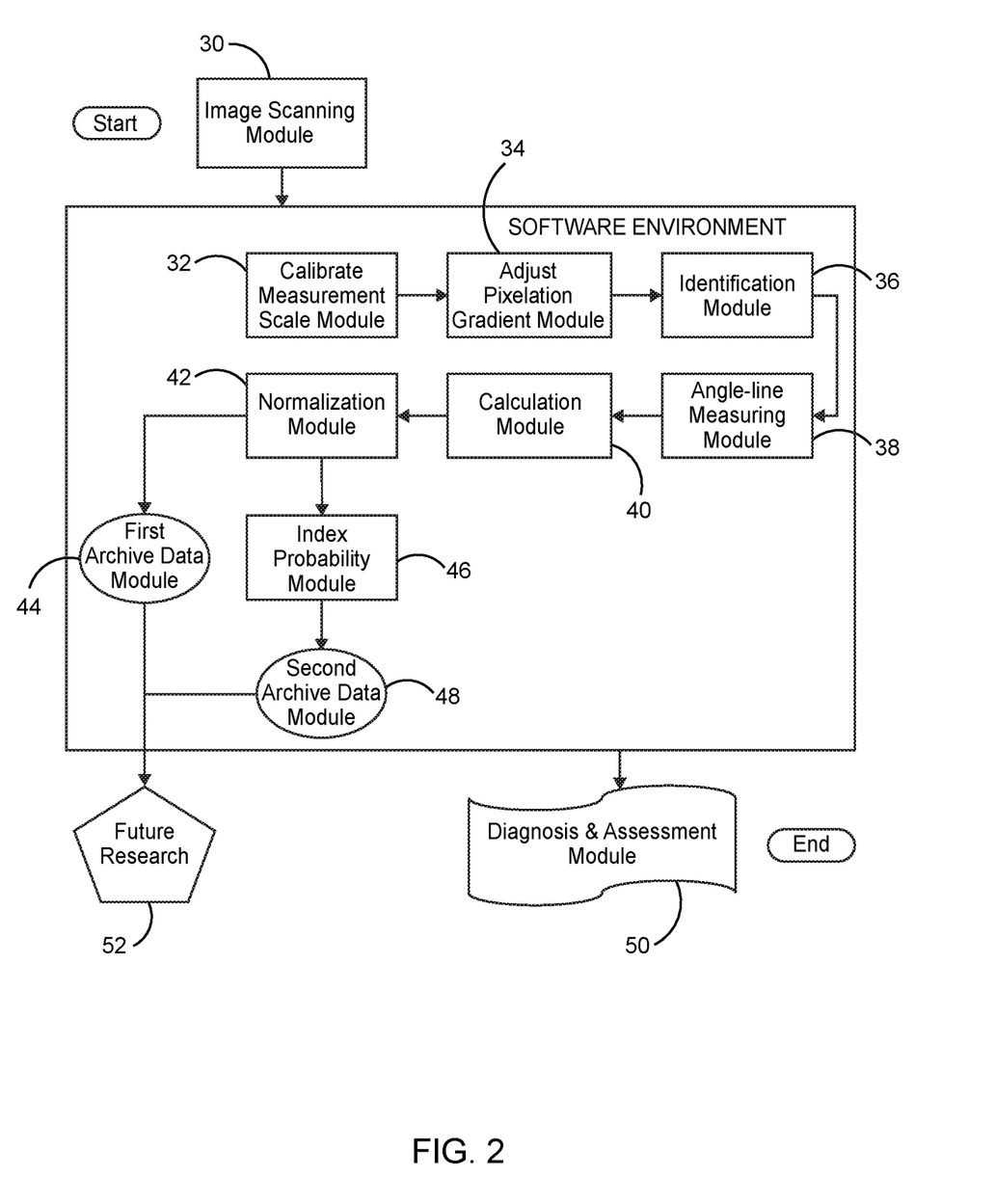
FIG. 2 illustrates a block diagram of a system for determining disc derangement disorders (DDD) in patients with temporomandibular joint disorders (TMD), in accordance with an embodiment of the present invention.

Referring to FIG. 2, a block diagram of a system 10 for determining the disc derangement disorders (DDD) in patients with the temporomandibular joint disorders (TMD) in accordance with an embodiment of the present invention is illustrated. The image scanning module 12 configured to provide the at least one image 14 of the TMJ of the patient into the DDD screening system 16 (See FIG. 1) via the disc derangement disorders (DDD) screening application 26. The disc derangement disorders (DDD) screening application 26 further comprises a calibrate measurement scale module 32, an adjust pixelation gradient module 34, an identification module 36, an angle-line measuring module 38, a calculation module 40, a normalization module 42, a first archive data module 44, an index probability module 46, a second archive data module 48 and a diagnosis and assessment module 50. The calibrate measurement scale module 32 and adjust pixelation gradient module 34 enables a measurement scale to calibrate a maximum pixelation level of at least one image 14 to provide an accurate measurement.

The identification module 36, the angle-line measuring module 38 and the calculation module 40 determines a measurable critical points and ratios of at least one image 14. The normalization module 42 generates a normalized measurement of the at least one image 14 and stores in the first archive data module 44. The normalization process involves geometrical standardization of a measurement protocol, which is factored into an index design and conversion of critical measurable components into proportions. The presence and absence of the disc derangement disorders (DDD) in the patients are evaluated by the index probability module 46 which provides a set of statistical probability data of the at least one image 14 and stores in the second archive data module 48 for generating a diagnosis and assessment report at the diagnosis and assessment module 50.

Figure 3A:
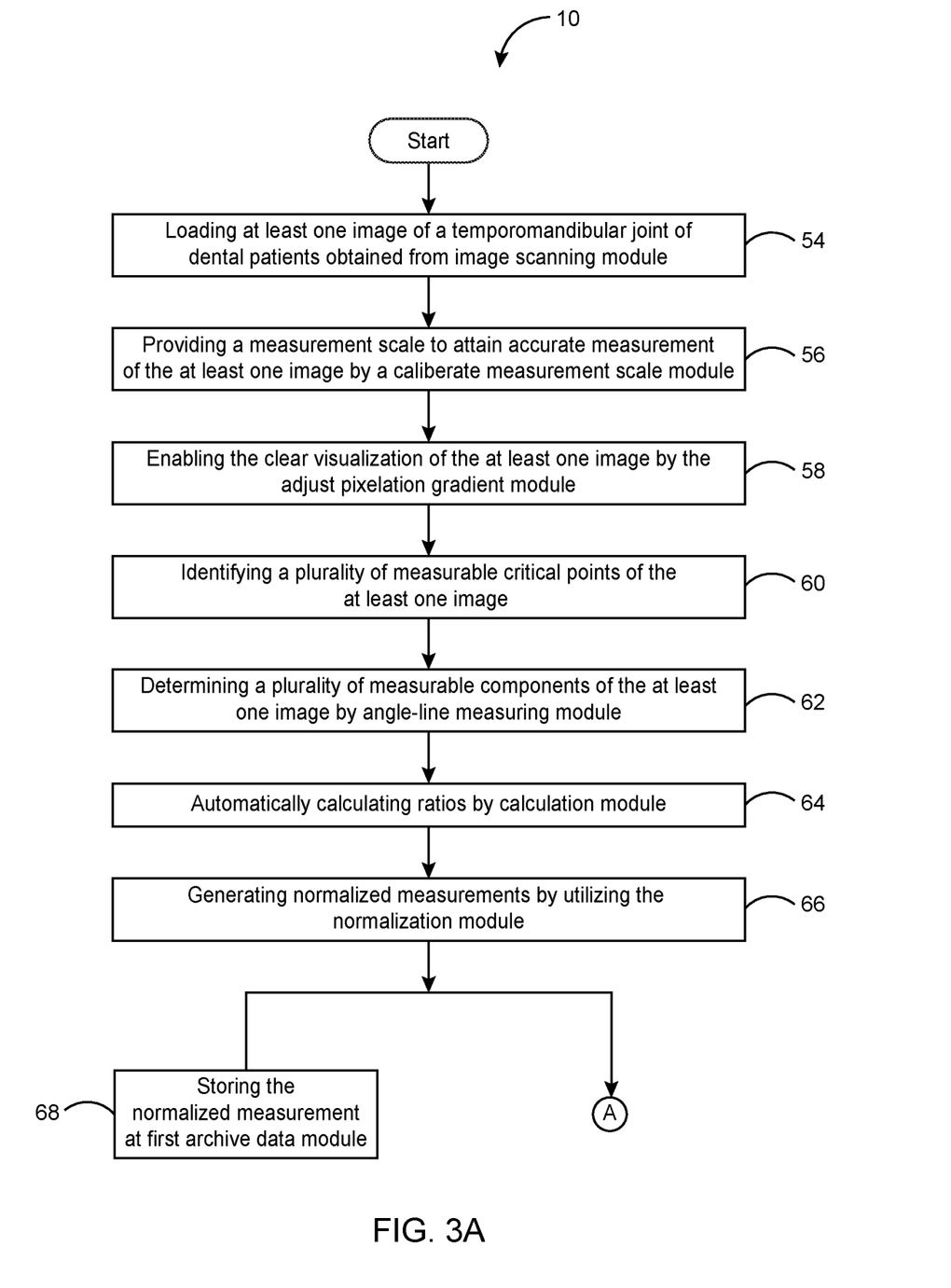
FIGS. 3A and 3B illustrate a flowchart of a method for determining disc derangement disorders (DDD) in patients with temporomandibular joint disorders (TMD), in accordance with an embodiment of the present invention.
Figure 3B:
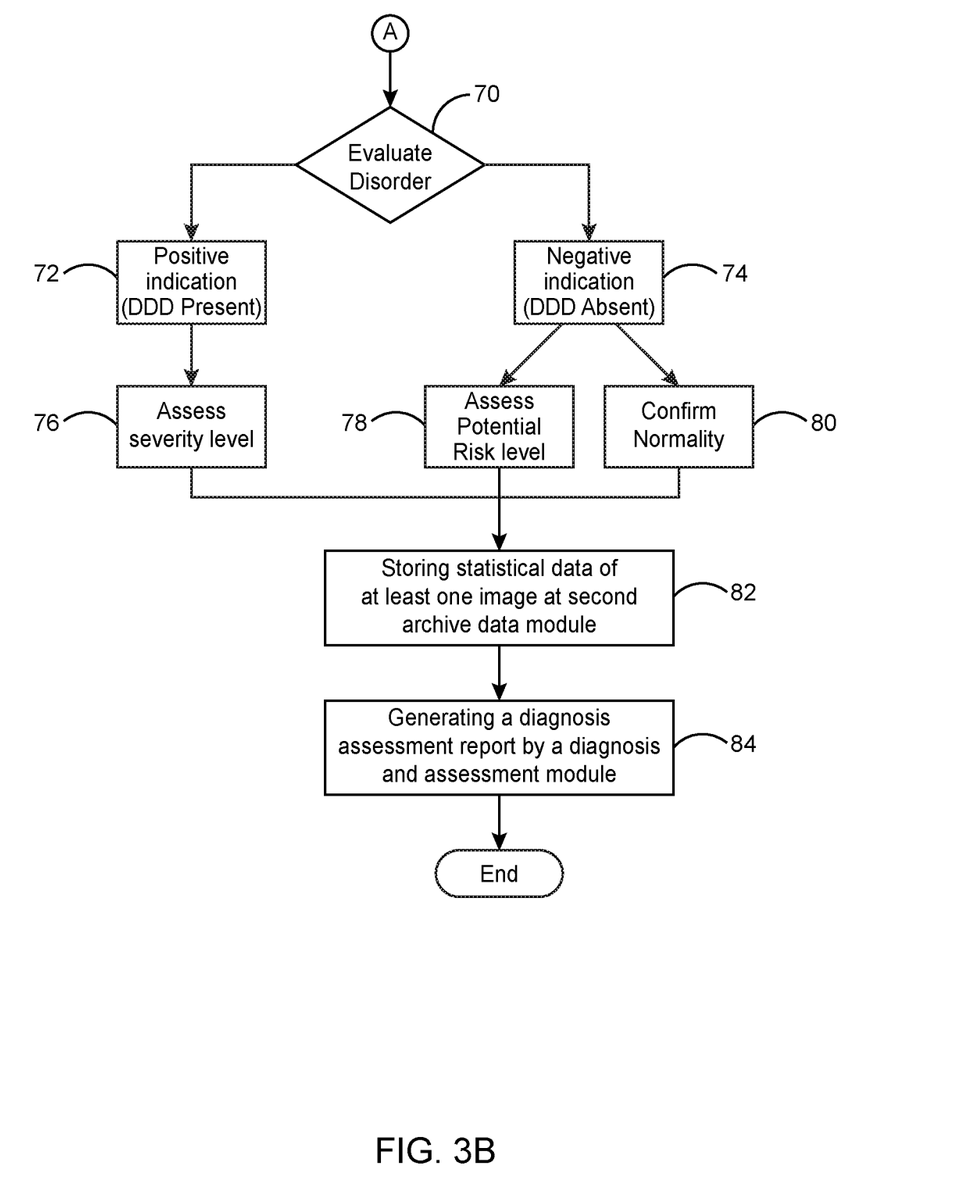

FIGS. 3A and 3B illustrate a flowchart of a method for determining disc derangement disorders (DDD) in patients with temporomandibular joint disorders (TMD) in accordance with an embodiment of the present invention. The method starts by providing the at least one image of the TMJ of the patient into the DDD screening system via the disc derangement disorders (DDD) screening application utilizing the image scanning module as indicated in block 54. The DDD screening system provides the measurement scale to attain an accurate measurement of the at least one image by the calibrate measurement scale module as indicated in block 56. The adjust pixelation gradient module enables the clear visualization of a horizontal line and a vertical line of the at least one image by adjusting pixelation as indicated in block 58. Identifying the plurality of measurable critical points for initiating automatic measurement of the at least one image as indicated in block 60.

The angle line measuring module measures the plurality of measurable components of the at least one image as shown in block 62. The calculation module allows the DDD screening system to automatically calculate ratios as indicated in block 64. The ratios include an anterior aspect of glenoid fossa height and width ratio, a posterior aspect of articular eminence width and height ratio, a mandibular condyle a mandibular condyle height and width ratio, a condylar head mediolateral dimension and anteroposterior dimension ratio and a mandibular condyle posterior angle and anterior angle ratio. The normalization module 42 generates a normalized measurement of the at least one image to assess unilateral and bilateral anterior disc displacement that pertaining to the morphology of an articular eminence, a glenoid fossa, and a mandibular condyle as indicated in block 66. The DDD screening application generates the normalized measurements, these are numbers that can be used to statistically evaluate the presence or absence of disc derangement disorders (DDD) based on an evidence-based research.

The first archive data module allows to store normalized measurement of the at least one image from the normalization module for further research purposes as indicated in the block 68. The DDD screening application allows the DDD screening system to evaluate disorder severity level assessment as indicated at block 70. In block 72 and 76, a positive indication in the statistical probability data shows the presence of DDD is likely and the severity level (low, medium, high) is then assessed is illustrated. In block 74, 78 and 80, a negative indication in the statistical probability data shows the absence of DDD is presumed, and the potential risk level (low, medium, high) of developing DDD is assessed and normal condition is confirmed. The set of statistical probability data of the at least one image to evaluate the presence and absence of the disc derangement disorders (DDD) in the dental patients are analyzed and stored in second archive data module as indicated in the block 82. The evaluation takes place on the basis of morphological differences of the TMJ in males and females. The DDD screening application can also produce an electronic signature, if encoded by the user. A diagnosis and assessment report is generated by analyzing the set of statistical probability data of the at least one image obtained from the index probability module as indicated at block 84. These statistical probability data, diagnosis and assessment report, can also be archived by the DDD screening application 26 along with any other pertinent information. In the diagnosis and assessment report, the user has the opportunity to include a narrative section to explain what the findings suggest and used to evaluate the presence or absence of DDD based on evidence-based research using statistical probabilities; and therefore, includes a diagnosis and multiple assessments for this type of TMD.

Figure 4A:
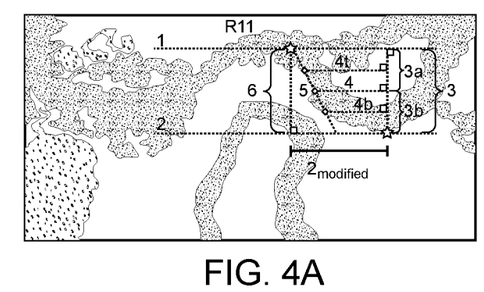
FIGS. 4A through 4C illustrate at least one image of the TMJ joint of the patient, in accordance with an embodiment of the present invention.
Figure 4B:
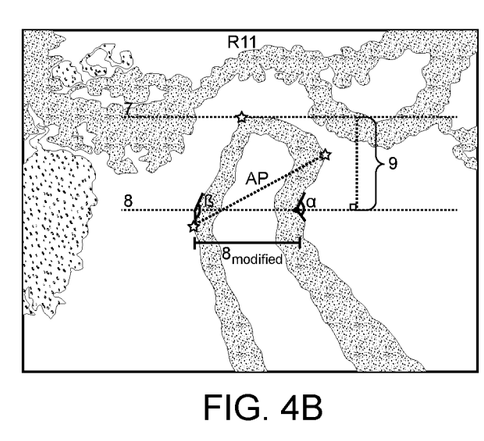
Figure 4C:
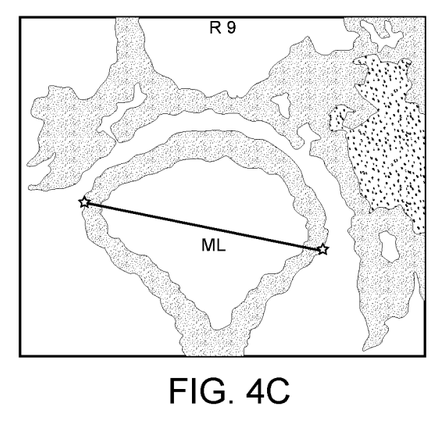
Figure 5A:
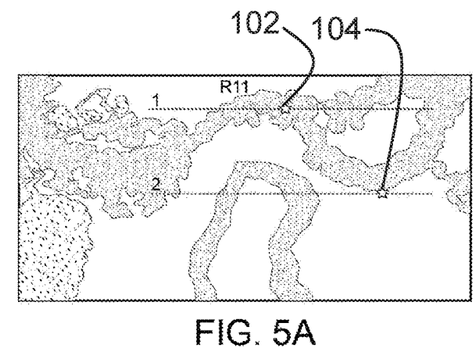
FIGS. 5A through 5G illustrate measurements of an articular eminence and a glenoid fossa, in the sagittal view, in accordance with the preferred embodiment of the present invention.
Figure 5B:
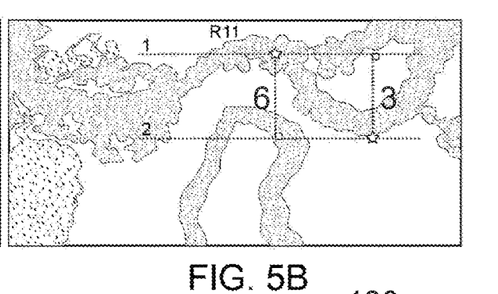
Figure 5C:
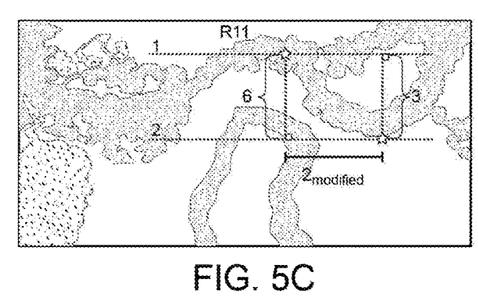
Figure 5D:
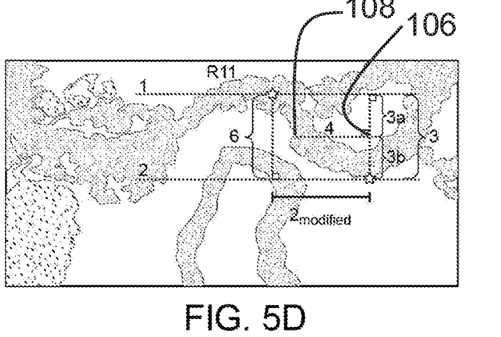
Figures 5E, 5F:
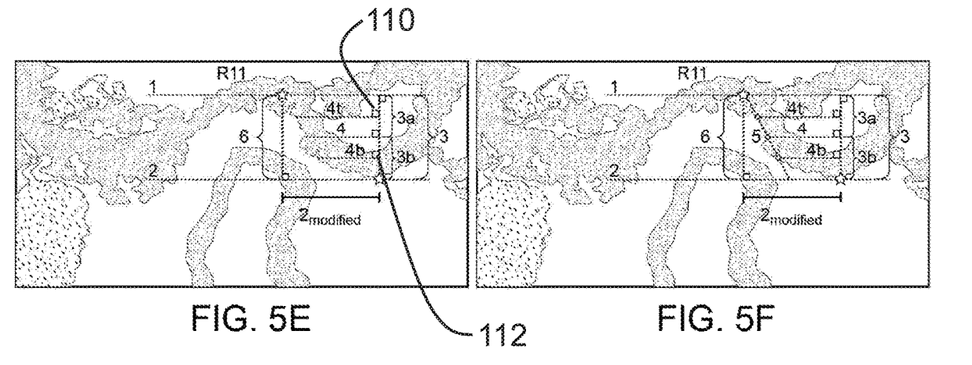
Figure 5G:
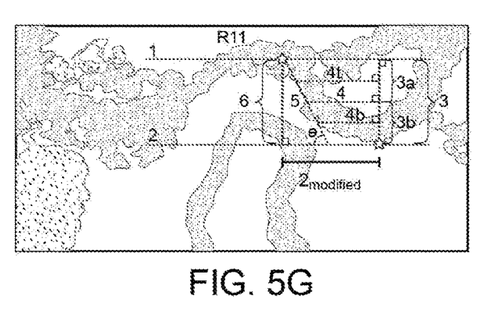

FIGS. 4A through 4C illustrate at least one image 14 of the TMJ joint of the patient, in accordance with the preferred embodiment of the present invention. The at least one image 14 of the TMJ is viewed in desired format (i.e., two from sagittal view and one from the coronal view). Further, the at least one image 14 is provided up to maximum pixelation of the at least one image 14 for a measurement and a clear visualization of horizontal and vertical lines while measurement taking. The DDD screening system 16 (See FIG. 1) generates a measurable index probability data, at the processor 20 (See FIG. 1) utilizes the normalized mathematical-based strategy to assess the unilateral/bilateral anterior disc displacement with/without reduction as it pertains to the morphology of an articular eminence, a glenoid fossa, and a mandibular condyle.

FIGS. 5A through 5G illustrate measurements of an articular eminence and a glenoid fossa, in the sagittal view, in accordance with the preferred embodiment of the present invention. The DDD screening system 16 (See FIG. 1) generates a measurable index probability data, at the processor 20 utilizes a normalized mathematical-based strategy to assess the morphology of an articular eminence and a glenoid fossa. On loading the at least one image 14 of the TMJ of the patient into the DDD screening application 26, at least one image 14 reaches its maximum pixelation level in order to clearly visualize horizontal and vertical lines while measurement taking. The DDD screening system 16 (See FIG. 1) identifies a superiormost point 102 of the glenoid fossa and an inferior most point 104 of the articular eminence in order to extend dotted horizontal lines from each of these designated points going in opposite directions and labeled as lines 1 and 2, respectively (See FIG. 5A).

The superiormost and inferiormost points 102, 104 identify the change of a direction at the glenoid fossa and articular eminence respectively. The lines 1 and 2 are verified parallel to each other by extending lines that are perpendicular to them from the designated points and labeled as lines 3 and 6 (See FIG. 5B). The lines 3 and 6 are measured and the horizontal distance between them is measured and labeled as line $2_{modified}$ (See FIG. 5C). The line 3 is bisected into the lines 3a and 3b (See FIG. 5D). The line perpendicular to line 3 extends from the midpoint 106 of line 3 to the outermost edge 108 of the articular eminence in the posterior direction and is measured and labeled as line 4 (See FIG. 5D). Lines 3a and 3b are each bisected, and from each new midpoint 110, 112, respectively, a new line perpendicular to line 3 extends to the outermost edge of the articular eminence in the posterior direction and are measured and labeled as lines 4t and 4b, respectively (See FIG. 5E). A line is drawn to connect all three points on the outermost edge of the articular eminence and is measured and labeled as line 5. The line 5 passes through the outermost edge of the line 4 and then possibly approximated between the lines 4t and 4b (See FIG. 5F). The angle between the lines 5 and 2 is measured and labeled as angle theta (See FIG. 5G).

Figures 6A, 6B:
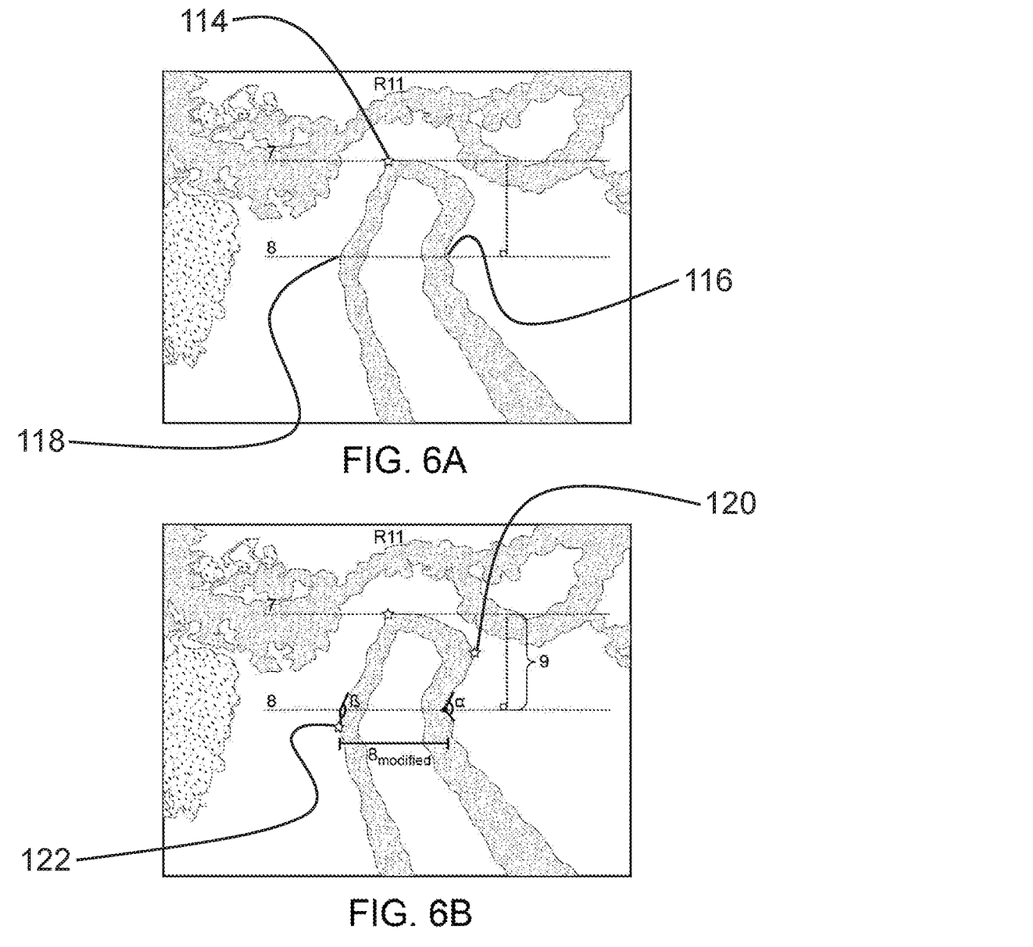
FIGS. 6A through 6C illustrate the measurements of a mandibular condyle in the sagittal view, in accordance with the preferred embodiment of the present invention.
Figure 6C:
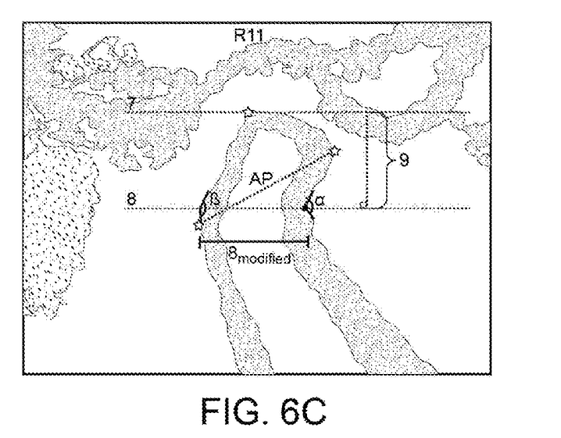

FIGS. 6A through 6C illustrate the measurements of a mandibular condyle in the sagittal view, in accordance with the preferred embodiment of the present invention. The DDD screening system 16 (See FIG. 1) generates the measurable in probability data, at the processor 20 utilizes a normalized mathematical-based strategy to assess the morphology of a mandibular condyle. On loading the at least one image 14 of a TMJ of the patient into the DDD screening application 26, the at least one image 14 reaches its maximum pixelation level in order to clearly visualize horizontal and vertical lines while measurement taking. The superiormost point 114 of the mandibular condyle is identified, and then a dotted horizontal line from this point is extended going in opposite directions and labeled as line 7. The innermost point 116 of the mandibular condyle concavity is identified in the anterior region; the DDD screening system 16 draws a horizontal line through this designated point going in both directions and labeled as line 8. The line 8 identifies a change in direction at the anterior region of the mandibular condyle. The lines 7 and 8 are verified parallel to each other by extending a line that is perpendicular to them. (See FIG. 6A).

The extended line that is perpendicular to lines 7 and 8 are measured and labeled as line 9. The angle at the innermost point 116 of the mandibular condyle concavity in the anterior region passing through the line 8 is measured and labeled as angle alpha (α). Similarly, the angle of the outermost point 118 of the mandibular condyle in the posterior region passing through the line 8 is measured and labeled as angle beta (β). The horizontal distance of line 8 between the outermost anterior and posterior points 116, 118, respectively, of the mandibular condyle, is measured and labeled as line $8_{modified}$ (See FIG. 6B). The outermost point 120 of the condylar head in the anterior region (above line 8) and the outermost point 122 of the mandibular condyle in the posterior region (above or below line 8) are identified, and then a line connecting these designated points is measured and labeled as line AP (See FIG. 6C). These outermost points identify a change in direction at the anterior and posterior regions of the mandibular condyle.

Figure 7:
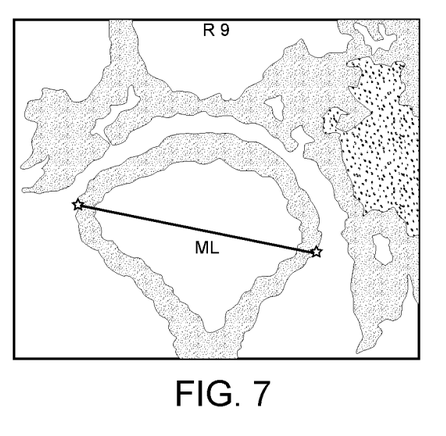
FIG. 7 illustrates a measurement of a mediolateral dimension of the mandibular condyle in the coronal view, in accordance with the preferred embodiment of the present invention.

FIG. 7 illustrates a measurement of a mediolateral dimension of the mandibular condyle in the coronal view, in accordance with the preferred embodiment of the present invention. The at least one image 14 of a TMJ of the patient is loaded into the DDD screening application 26, the at least one image 14 reaches its maximum pixelation level in order to clearly visualize horizontal and vertical lines while measurement taking. The medial-most and lateral-most points of the mandibular condyle are identified and a line connecting these designated points is measured and labeled as line ML. The medial-most and lateral-most points identify a change in direction at the medial and lateral regions, respectively, of the condylar head.

Figure 8:
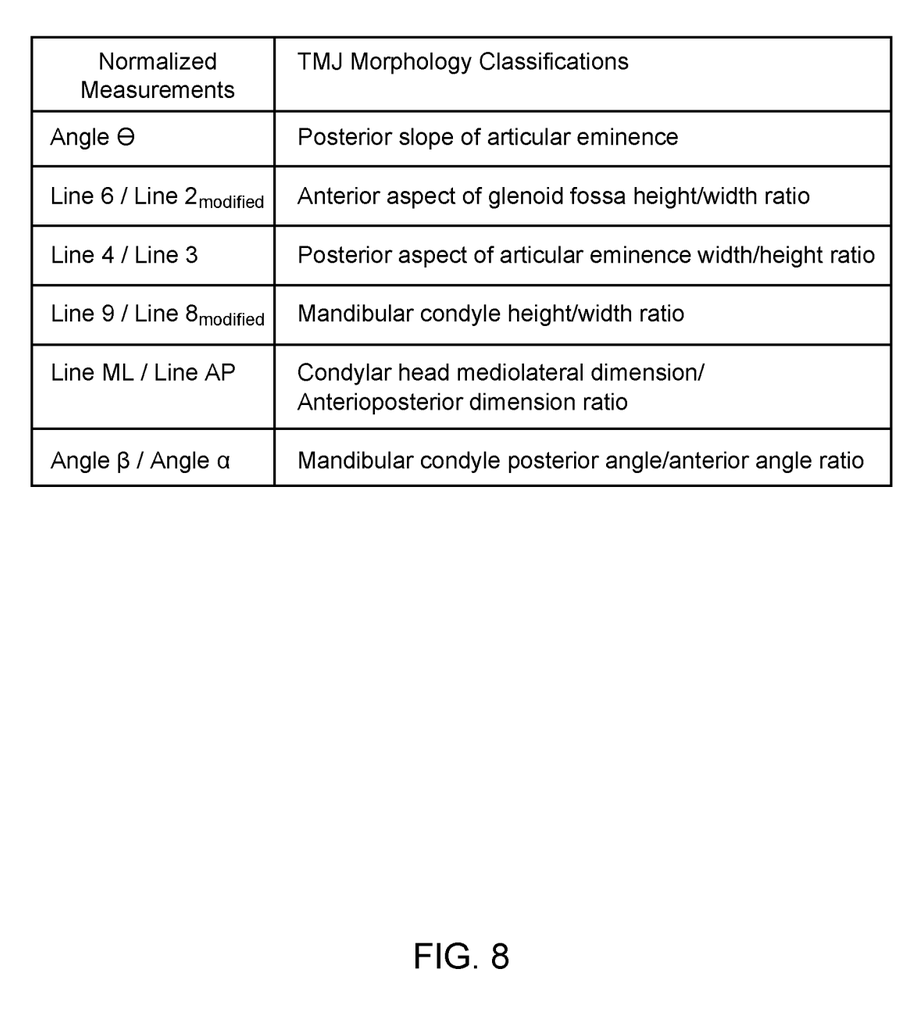
FIG. 8 shows a table illustrating the relationship between normalized measurements and TMJ morphology classifications assessed in accordance with the preferred embodiment of the present invention.

FIG. 8 shows a table illustrating the relationship between a measurement components and a plurality of dependent variables assessed in accordance with the preferred embodiment of the present invention. The measurable index presented in the DDD screening application 26 utilizes an interdependent mathematical strategy to assess the morphology of the articular eminence, the glenoid fossa, and the mandibular condylein relationship to each other. The measureable components (lines and angles) are normalized to permit reliable comparison between individuals or among groups to be considered. The normalization process involves geometrical standardization of the measurement protocol, which is factored into the index design, and conversion of critical measureable components into proportions. The gender plays a significant role in a S*R interaction for the DDD screening system 16. In other words, the levels of reduction (with or without) and symmetry (unilateral or bilateral paired with like verses bilateral paired with non-like) interact with each other to influence the dependent variables in specific ways. The dependent variables include the posterior slope of the articular eminence, the anterior aspect of the glenoid fossa height/width ratio, the posterior aspect of the articular eminence width/height ratio, the mandibular condyle height/width ratio, the condylar head mediolateral (ML) dimension/anteroposterior (AP) dimension ratio, and the mandibular condyle posterior angle/anterior angle ratio. The significance of the S*R interaction is recognized when gender was factored into the study design as the third factor with two levels: males and females. The differences between males and females are evaluated in two-way interaction between the two factors: symmetry and reduction. The morphological features of the TMJ to consider in DDD are the posterior slope of the articular eminence, the dimensions of the condylar head, namely its height/width as well as ML/AP dimensions, and the contour of the condylar neck, defined as the posterior angle/anterior angle of the mandibular condyle. The measurable index probability data allows the system 10 (See FIG. 1) to evaluate a contour of a condylar neck, a plurality of dimensions of a condylar head and a glenoid fossa, and a posterior slope of an articular eminence based on morphological differences of the TMJ in males and females with anterior disc displacement.

Figure 9:
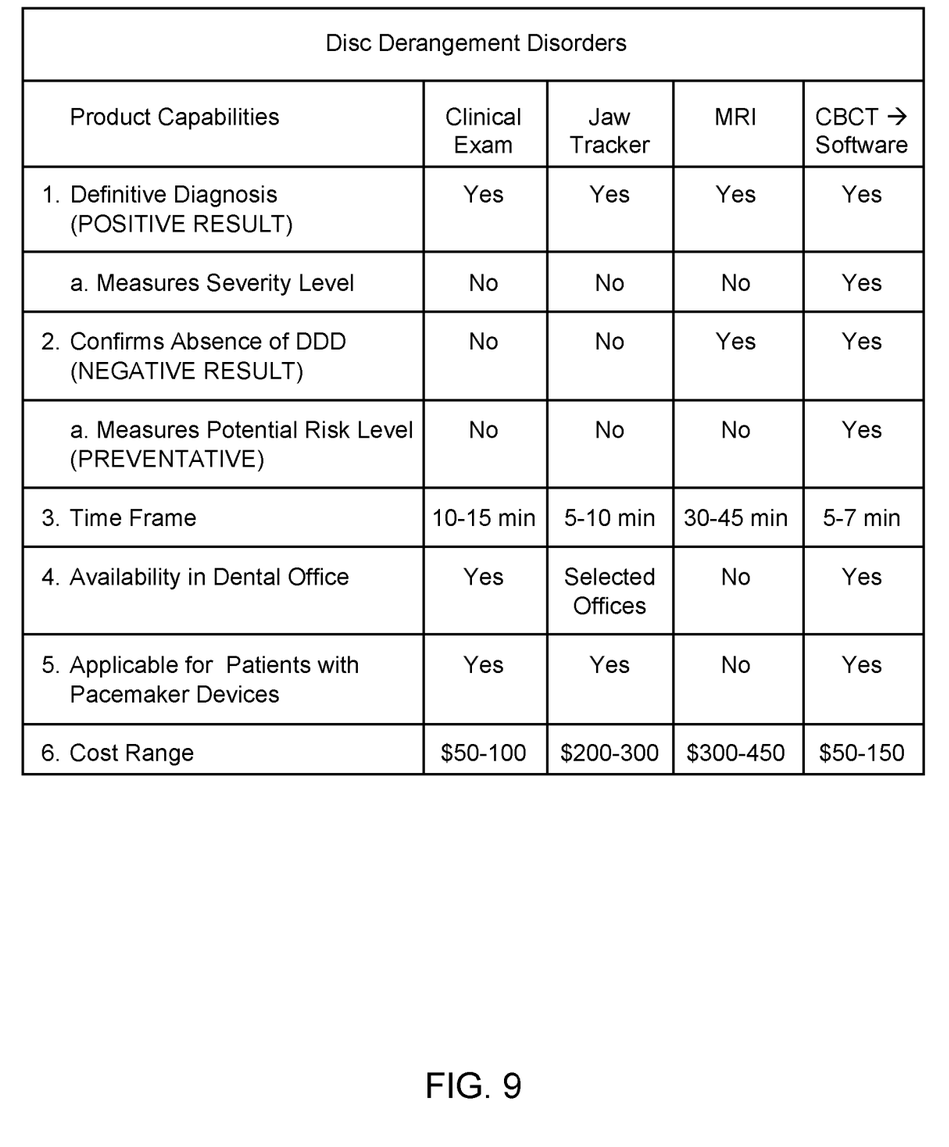
FIG. 9 shows a table illustrating the comparison of product capabilities between the DDD screening system with other products in accordance with the preferred embodiment of the present invention.

FIG. 9 shows a table illustrating the comparison of product capabilities between the DDD screening system 16 with other products in accordance with the preferred embodiment of the present invention. The DDD screening application 26 provides a practical approach to screen for DDD by simply uploading the at least one image 14 into the DDD screening application 26 and letting the DDD screening application 26 to do the work. The diagnosis and assessment report generated is reviewed by the user and adds a narrative portion to explain what the findings indicate. The DDD screening application 26 also offers the patient the added benefit of convenience since these screenings can be done during a routine dental visit. The DDD screening application 26 can encompass a wider range of dental patients and is not patient-limiting. The symptomatic patients who present with pain, joint clicking, or mouth deviation during opening often tend to seek treatment, and therefore, are likely to be clinically examined for DDD. The available treatments do not resolve the patient's TMD symptoms. The additional diagnostic measures, such as jaw tracker or magnetic resonance imaging (MRI), are utilized. A jaw tracker tracks movements of the mandible (lower jaw) three dimensionally, as it traverses through space, and can be used to help diagnose TMD, whereas, MRI is used to visualize soft tissue structures, such as the disc of the TMJ, and traditionally is known to provide a definitive diagnosis for DDD If the disc is not situated in its normal position relative to the bony structures (condyle and mandibular fossa). Unlike MRI, the use of CBCT to acquire images for the DDD screening application 26 uses does not exclude patients with pacemaker devices and only takes about five minutes. CBCT are generally less expensive than MRI. The DDD screening application 26 can identify those patients and measure the severity level of the disorder. This is also true for symptomatic patients. None of the other available products or methods on the market can quantify the severity of this pathological condition. By detecting DDD in its early stages, as would be detected by a low to medium severity levels, the examiner is then able to therapeutically intervene to potentially arrest the progression of this pathological disorder, even if the patient is asymptomatic. These therapeutic measures might include potentially arresting or preventing the onset of a variety of inflammatory disorders (since TMD has been suggested to cause osteoarthritis, also known as degenerative joint disease) and/or establishing orthopedic stability of the TMJ by incorporating occlusal adjustment measures in the restorative phase of dental treatment planning.

In addition, DDD screening application 26 can also quantify the potential risk level of developing this disorder if there is a negative indication for DDD. This preventative capability, which is not a feature of the other products or methods on the market, enables the dental professional to intervene and potentially prevent the onset of DDD. The preventative nature of this DDD screening application 26 can help minimize future dental expense burden attributed to DDD treatment costs experienced by patients and insurance companies alike.

The preventative, cost-effective, practical and convenient approach of the DDD screening application 26 to statistically measure the levels of severity and potential risk for disc derangement disorders makes this product a comprehensive tool for the diagnosis and assessment of DDD. These DDD screening application 26 capabilities will allow the dental professional to offer the patient the best treatment options available tailored to the patient's own assessments.

While a particular form of the invention has been illustrated and described, it will be apparent that various modifications can be made without departing from the spirit and scope of the invention. Accordingly, it is not intended that the invention be limited, except as by the appended claims.

What is claimed is:

1. A non-transitory computer-readable medium, having stored thereon, instructions that when executed by a computing device, cause the computing device to perform operations for determining disc derangement disorder variables in a patient, the operations comprising:
(A) scanning with an image scanner and inputting a first image of a first patient's articular eminence and glenoid fossa;
(B) on the first image:
(B)(1) identifying a superior-most point of the glenoid fossa and an inferior-most point of the articular eminence;
(B)(2) overlaying a first horizontal line through the superior-most point of the glenoid fossa identified in (B)(1) and a second horizontal line through the inferior-most point of the articular eminence identified in (B)(1);
(B)(3) overlaying and measuring a length of a first vertical line that extends between the first and second horizontal lines overlaid in (B)(2) originating at the superior-most point of the glenoid fossa identified in (B)(1);
(B)(4) overlaying and measuring a length of a second vertical line that extends between the first and second horizontal lines overlaid in (B)(2) originating at the inferior-most point of the articular eminence identified in (B)(1); and
(B)(5) measuring a horizontal distance between the first vertical line overlaid in (B)(3) and the second vertical line overlaid in (B)(4);
(C) calculating at least one disc derangement disorder variable by:
(C)(1) dividing the measured length of the first vertical line measured in (B)(3) by the horizontal distance measured in (B)(5) to determine a first disc derangement disorder variable including an anterior aspect of the glenoid fossa height to width ratio;
(D) using the at least one disc derangement disorder variable to tailor the dental treatment of the first patient.

2. The non-transitory computer-readable medium of claim 1 further comprising:
(B)(6) determining a midpoint of the second vertical line overlaid in (B)(4); and
(B)(7) overlaying and measuring a length of a third horizontal line originating at the midpoint determined in (B)(6) and extending to a first outermost edge of the articular eminence in a posterior direction; and
wherein the calculating of at least one disc derangement disorder variable in (C) includes:
(C)(2) dividing the length of the third horizontal line measured in (B)(7) by the length of the second vertical line measured in (B)(4) to determine a second disc derangement disorder variable including the posterior aspect of the articular eminence width to height ratio.

3. The non-transitory computer-readable medium of claim 2 further comprising operations of:
- (B)(8) determining a first-quarter point of the second vertical line overlaid in (B)(4) and a third-quarter point of the second vertical line overlaid in (B)(4);
- (B)(9) overlaying and measuring a length of a fourth horizontal line originating at the first-quarter point determined in (B)(8) and extending to a second outermost edge of the articular eminence in the posterior direction, and overlaying and measuring the length of a fifth horizontal line originating at the third-quarter point determined in (B)(8) and extending to a third outermost edge of the articular eminence in the posterior direction;
- (B)(10) overlaying and measuring a length of a line that extends between the first and second horizontal lines overlaid in (B)(2), that originates at the superior-most point of the glenoid fossa identified in (B)(1) and that extends through a furthermost posterior point of each of the third and fourth horizontal lines overlaid in (B)(9) and a furthermost posterior point of the third horizontal line overlaid in (B)(7); and
- (B)(11) measuring an angle between the line overlaid in (B)(10) and the second horizontal line overlaid in (B)(2) through the inferior-most point of the articular eminence; and
- wherein the calculating of at least one disc derangement disorder variable in (C) includes:
- (C)(3) identifying the angle measured in (B)(11) as a third disc derangement disorder variable including a posterior slope of the articular eminence.

4. The non-transitory computer-readable medium of claim 1 further comprising operations of:
- (E) storing the calculated at least one disc derangement disorder variable to memory.

5. The non-transitory computer-readable medium of claim 1 wherein the image scanner includes a cone beam computed tomography (CBCT) scanner.

6. A non-transitory computer-readable medium, having stored thereon, instructions that when executed by a computing device, cause the computing device to perform operations for determining disc derangement disorder variables in a patient, the operations comprising:
- (A) scanning with an image scanner and inputting a first image of a first patient's mandibular condyle;
- (B) on the first image:
  - (B)(1) identifying a superior-most point of the mandibular condyle;
  - (B)(2) overlaying one horizontal line through the point identified in (B)(1);
  - (B)(3) identifying an innermost point of a mandibular condyle concavity in an anterior region;
  - (B)(4) overlaying one horizontal line through the point identified in (B)(3);
  - (B)(5) measuring an angle of the mandibular condyle concavity in the anterior region at the innermost point identified in (B)(3);
  - (B)(6) identifying an outermost point of the mandibular condyle in a posterior region that falls on the horizontal line overlaid in (B)(4); and
  - (B)(7) measuring an angle of the mandibular condyle concavity in the posterior region at the outermost point identified in (B)(6); and
- (C) calculating at least one disc derangement disorder variable by:
  - (C)(1) dividing the angle measured in (B)(7) by the angle measured in (B)(5) to determine a first disc derangement disorder variable including a mandibular condyle posterior angle and anterior angle ratio;
- (D) using the at least one disc derangement disorder variable to tailor the dental treatment of the first patient.

7. The non-transitory computer-readable medium of claim 6 further comprising operations of:
- (B)(8) measuring a distance between the innermost point identified in (B)(3) and the outermost point identified in (B)(6) along the horizontal line overlaid in (B)(4);
- (B)(9) overlaying and measuring a length of a first vertical line that extends between the horizontal lines overlaid in (B)(2) and (B)(4); and
- wherein the calculating of at least one disc derangement disorder variable in (C) includes:
- (C)(2) dividing the length of a first vertical line measured in (B)(9) by the distance measured in (B)(8) to determine a second disc derangement disorder variable including a mandibular condyle height to width ratio.

8. The non-transitory computer-readable medium of claim 7 further comprising operations of:
- (B)(10) identifying an outermost point of a condylar head in the anterior region above the horizontal line overlaid in (B)(4) and the outermost point of the mandibular condyle in the posterior region, and overlaying a line between the two points;
- (B)(11) measuring the distance between the outermost point of the condylar head in the anterior region and the outermost point of the mandibular condyle in the posterior region along the line overlaid in (B)(10);
- (B)(12) inputting a second image of the first patient's mandibular condyle in a coronal view;
- (B)(13) identifying a medial-most point of the mandibular condyle in the second image;
- (B)(14) identifying a lateral-most point of the mandibular condyle in the second image; and
- (B)(15) overlaying and measuring a length of a line extending between the points identified in (B)(14) and (B)(15);
- wherein the calculating of at least one disc derangement disorder variable in (C) includes:
- (C)(3) dividing the length of the line measured in (B)(15) by the distance measured in (B)(11) to determine a third disc derangement disorder variable including a condylar head mediolateral dimension and anteroposterior dimension ratio.

9. The non-transitory computer-readable medium of claim further comprising:
- (E) storing the calculated at least one disc derangement disorder variable to memory.

10. The non-transitory computer-readable medium of claim 6 wherein the image scanner includes a cone beam computed tomography (CBCT) scanner.

* * * * *